US008067467B2

(12) United States Patent
Joshi et al.

(10) Patent No.: US 8,067,467 B2
(45) Date of Patent: Nov. 29, 2011

(54) THIOSUCCINIC ACID DERIVATIVES AND THE USE THEREOF

(75) Inventors: Rajendra Kumar Joshi, Zürich (CH); Hans-Peter Strebel, Muri (CH); Jitka Ulrichová, Olomouc (CZ); Thomas J. Schmidt, Havixbeck (DE)

(73) Assignee: Biogen Idec International GmbH, Zug (CH)

( * ) Notice: Subject to any disclaimer, the term of this patent is extended or adjusted under 35 U.S.C. 154(b) by 631 days.

(21) Appl. No.: 11/914,426

(22) PCT Filed: May 3, 2006

(86) PCT No.: PCT/EP2006/004134
§ 371 (c)(1),
(2), (4) Date: May 23, 2008

(87) PCT Pub. No.: WO2006/122652
PCT Pub. Date: Nov. 23, 2006

(65) Prior Publication Data
US 2009/0011986 A1 Jan. 8, 2009

(30) Foreign Application Priority Data

May 18, 2005 (DE) .......................... 10 2005 022 845

(51) Int. Cl.
*A61K 31/225* (2006.01)
*C07C 323/02* (2006.01)
(52) U.S. Cl. .......................... 514/547; 560/153; 560/154
(58) Field of Classification Search .......................... None
See application file for complete search history.

(56) References Cited

U.S. PATENT DOCUMENTS 3,345,327 A 10/1967 Dexter et al.
2004/0038889 A1 2/2004 Joshi et al.

FOREIGN PATENT DOCUMENTS

EP 579222 A2 * 1/1994
WO WO 9402445 A1 * 2/1994

OTHER PUBLICATIONS

Ailman, "Synthesis of O, O-Dimethyl S-(1,2-Dicarbethoxy) ethyl Phosphorothioate (Maloxon) and Related Compounds from Trialkyl Phosphites and Organic Disulfides," *Journal of Organic Chemistry*, 30(4): 1074-1077(1965).
Brophy et al., "β-Carbonyl Substituted Glutathione Conjugates as Inhinitors of O. Volvulus GST2," *Bioorganic & Medicinal Chemistry Letters*, 10(9): 979-981 (2000).
Cui et al., "Metabolism of the Nephrotoxicant N-(3,5-Dichlorophenyl) succinmide in Rats: Evidence for Bioactivation Through Alcohol-O-glucuronidation and O-Sulfaction," *Chemical Research in Toxicology*, 18(6): 991-1003 (2005).

Endo et al., "Anionic 3,4-Diaza [3,3] Sigmatropic Rearrangements of N,N'-Diacylhydrazines," *Tetrahedron Letters*, 32(35): 4517-4520 (1991).
Fushiya et al., "(2R), (1'R) and (2R), (1'S)-2-Amino-3-(1,2-dicarboxyethylthio) propanoic Acids from *Amanita pantherina*, Antagonists of N-Methyl-D-aspartic Acid (NMDA) Receptors," *Chemical & Pharmaceutical Bulletin*, 41(3): 484-486 (1993).
Henesey et al., "Renal Damage, Metabolism and Covalent Binding Following Administration of the Nephrotoxicant N-(3,5-Dichlorophenyl) Succinimide (NDPS) to Male Fischer 344 Rats," *Toxicology*, 170(3): 187-200 (2002).
McKay et al., "By-Product Analogues for Bovine Carboxypeptidase B," *American Chemical Society*, 17(3): 401-405 (1978).
Neumann et al., "Peptide Liposomes from Amphiphilic Amino Acids," *American Chemical Society*, 108(30): 487-490 (1986).
Pacanis et al., "Studies on Chemical and Enzymatic Synthesis of Maleyl-CoA," *The Journal of Biological Chemistry*, 256(24): 13030-13034 (1981). Sakaue et al., "Physiological Activities of S-(1,2-Dicarboxyethyl) glutathione as an Intrinsic Tripeptide Present in Liver, Heart and Lens," *Arzneimittel-Forschung, Drug Research*, 42(12): 1482-1486 (1992).
Written Opinion mailed Jan. 16, 2007, for International Application No. PCT/EP2006/004134, filed May 3, 2006.
International Search Report mailed Jan. 16, 2007, for International Application No. PCT/EP2006/004134, filed May 3, 2006.
International Preliminary Examination Report completed May 9, 2007, for International Application No. PCT/EP2006/004134, filed May 3, 2006.

* cited by examiner

*Primary Examiner* — Jeffrey E Russel
(74) *Attorney, Agent, or Firm* — Sterne, Kessler, Goldstein & Fox P.L.L.C.

(57) ABSTRACT

The present invention relates to compounds of the formula (I) wherein $X_1$ and $X_2$ independently represent O, NH or S, $R_1$ and $R_2$ are independently selected from the group consisting of a $C_1$-$C_{30}$ hydrocarbyl group, an amino acid bonded via an amide bond or a peptide bonded via an amide bond each having up to 200 amino acids, the conjugated residue $X_1$ or $X_2$ in this case being NH, and hydrogen, both radicals $R_1$ and $R_2$ preferably not being H, wherein $R_3$ is a residue selected from group consisting of —S—$R_6$, wherein $R_6$ is a $C_1$-$C_{30}$ hydrocarbyl group, at least one of $R_1$ and $R_2$ not being H when $X_1$ and $X_2$ are oxygen, —S—$CH_2$—CH($NH_2$)(COOH) (cysteine-S-yl), a homologue or derivative (e.g. N-acetyl cysteine-S-yl) thereof, a peptide having up to 200 amino acids which contains at least one amino acid radical with a thiol group, preferably a cysteine radical, and is bonded via the thio sulfur, preferably via the cysteine sulfur (peptide-S-yl), coenzyme A which is bonded via a thiol group or fragments thereof, acyl carrier protein bonded via a thiol group, and dihydrolipoic acid bonded via a thiol group, and pharmaceutically acceptable salts thereof. The present invention also relates to the use of these compounds for preparing a drug and drugs containing the same.

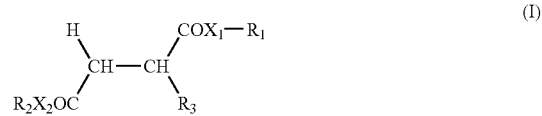

(I)

11 Claims, 3 Drawing Sheets

SEQUENCE LISTING

<160> NUMBER OF SEQ ID NOS: 4

<210> SEQ ID NO 1
<211> LENGTH: 16
<212> TYPE: PRT
<213> ORGANISM: Artificial Sequence
<220> FEATURE:
<223> OTHER INFORMATION: peptide which may be derived from peptide and
      or fragment by homologous substitution or deletion or insertion
      of one or more amino acid or acids into or from the peptide chain

<400> SEQUENCE: 1

Cys Arg Gly Gln Gly Thr Ala Ser Ser Gly Asn Val Ser Asp Leu Ala
1               5                   10                  15

<210> SEQ ID NO 2
<211> LENGTH: 13
<212> TYPE: PRT
<213> ORGANISM: Artificial Sequence
<220> FEATURE:
<223> OTHER INFORMATION: peptide which may be derived from peptide and
      or fragment by homologous substitution or deletion or insertion
      of one or more amino acid or acids into or from the peptide chain

<400> SEQUENCE: 2

Arg Val Ser Leu Ala Gly Ala Cys Gly Val Gly Gly Tyr
1               5                   10

<210> SEQ ID NO 3
<211> LENGTH: 9
<212> TYPE: PRT
<213> ORGANISM: Artificial Sequence
<220> FEATURE:
<223> OTHER INFORMATION: peptide which may be derived from peptide and
      or fragment by homologous substitution or deletion or insertion
      of one or more amino acid or acids into or from the peptide chain

<400> SEQUENCE: 3

Ile Gln Gln Gln Arg Ala Met Leu Cys
1               5

<210> SEQ ID NO 4
<211> LENGTH: 42
<212> TYPE: PRT
<213> ORGANISM: Artificial Sequence
<220> FEATURE:
<223> OTHER INFORMATION: peptide which may be derived from peptide and
      or fragment by homologous substitution or deletion or insertion
      of one or more amino acid or acids into or from the peptide chain

<400> SEQUENCE: 4

Lys Pro Asn Val Thr Pro Thr Val Ala His Arg Thr Ser Ser Ser Arg
1               5                   10                  15

Val Ala Val Arg Ser Leu Val Glu Phe Thr Cys Cys Arg Ala Gly Ala
                20                  25                  30

Leu Asp Trp Val Cys Ala Arg Arg Gly Arg
            35                  40

THIOSUCCINIC ACID DERIVATIVES AND THE USE THEREOF

This application claims priority to PCT International Application No. PCT/EP2006/004134 filed May 3, 2006, now International Publication No. WO 2006/122652, which claims priority to German Patent Application No. DE 10 2005 022 845.3 filed May 18, 2005, both of which are incorporated by reference herein for all purposes.

The present invention relates to thiosuccinic acid derivatives and the use thereof for preparing a drug as well as drugs containing these derivatives.

For a long time, fumaric acid dialkyl esters, fumaric acid monoalkyl esters and salts thereof have been successfully used for treating psoriasis. Said use is described in a number of patents, for example EP-B-0 312 697.

The use of fumaric acid mono- and diesters is also described for the treatment of autoimmune diseases such as polyarthritis, also called rheumatoid arthritis, or multiple sclerosis (cf. DE 197 21 099.6 and DE 198 53 487.6), but also for use in transplantation medicine (cf. DE 198 53 487.6 and DE 198 39 566.3). The use of fumaric acid mono- and diesters for the treatment of NF-kappaB mediated diseases such as the treatment of mitochondrial diseases is also known from DE 101 01 307.8 and DE 100 00 577.2. All of the cited documents describe fumaric acid mono- and diesters, optionally in the form of certain salts.

Because of their volatility or sublimability, however, the above-mentioned fumaric acid esters have the disadvantage of being difficult to handle when preparing pharmaceutical products, especially those in solid form for oral administration. Specifically, the preparation of such products requires protective measures such as the use of breathing masks, gloves, protective clothing, etc.

In addition, the fumaric acid esters are absorbed in the gastro-intestinal tract after oral administration and taken up unspecifically from the bloodstream by all body cells. Therefore, it is necessary to administer high dosages. Such high dosages in turn lead to the known side effects of a fumaric acid therapy like flush symptoms (reddening) or gastrointestinal irritation (nausea, diarrhoea, winds). Even though such side effects may be reduced considerably by administering the active ingredient in the form of micro-tablets as described in the above-cited prior art, they cannot be avoided altogether.

At the same time, the fumaric acid esters are rapidly hydrolysed in the blood and the products of said hydrolysis, alcohol and fumaric acid or fumaric acid monoester, metabolised. In order to maintain therapeutically effective levels repeated administration is therefore necessary. Even though a certain adaptation is observed concerning the side effects upon repeated administration, a further reduction of the side effect rate would be desirable.

In order to avoid these disadvantages fumaric acid mono- and -diamides have been used as known from DE 101 33 004. These amides are formed with amino acids and preferably with certain peptides. Binding them to a peptide also permits specifically transporting the fumaric acid derivative to individual target cells. However, the above-mentioned fumaric acid amide derivatives have the disadvantage of being expensive to produce.

In addition, DE 102 17 314.1 has proposed carbocyclic and oxacarbocyclic fumaric acid oligomers. This patent relates to carbocyclic and oxacarbocyclic fumaric acid oligomers comprising 2 to 10 units derived from fumaric acid and/or esters and/or amides thereof as repeating units. Such fumaric acid derivatives are more stable against hydrolysis, easier to produce than the amides and less difficult to handle than fumaric acid esters and salts thereof.

First of all, the above-mentioned fumaric acid derivatives have the disadvantage of having a pKa in the acidic range. Secondly, they hydrolyse quickly, releasing the fumaric acid basic skeleton or a pertinent monoester. Both properties contribute to the known side effects of a fumaric acid therapy such as flushing and gastrointestinal problems upon oral administration.

Therefore, it is an object of the present invention to provide compounds which are easy to prepare, well tolerated and more resistant to hydrolysis and which, at the same time, may be administered by any desired route. In particular, it is intended to administer the fumaric acid derivatives by the parenteral route (by injection).

SUMMARY OF THE INVENTION

This objective is achieved by a number of thiosuccinic acid derivatives. The applicant has found surprisingly that the effect of such substances is similar to that of fumaric acid derivatives. The inventors assume that this is due to the conversion of the thiosuccinic acid derivatives to the active fumaric acid derivatives under physiological conditions. In a first aspect, the present invention therefore relates to compounds of the formula (I)

wherein $X_1$ and $X_2$ independently represent O, NH or S, $R_1$ and $R_2$ are independently selected from the group consisting of a $C_1$-$C_{30}$ hydrocarbyl group, an amino acid bonded via an amide bond or a peptide bonded via an amide bond each having up to 200 amino acids, the residue $X_1$ or $X_2$ conjugated to $R_1$ or $R_2$, respectively, in this case being NH, and hydrogen, one of the radicals $R_1$ and $R_2$ preferably not being H, wherein $R_3$ is a residue selected from the group consisting of —S—$R_6$, wherein $R_6$ is a $C_1$-$C_{30}$ hydrocarbyl group, not both of $R_1$ and $R_2$ being H when $X_1$ and $X_2$ are oxygen, —S—$CH_2$—$CH(NH_2)(COOH)$ (cysteine-S-yl), a homologue or derivative (e.g. N-acetyl cysteine-S-yl) thereof, a peptide having up to 200 amino acids which contains at least one amino acid radical, preferably a cysteine radical with a thiol group, and is bonded via the thio sulfur, preferably via the cysteine sulfur (peptide-S-yl), coenzyme A which is bonded via a thiol group or fragments thereof, acyl carrier protein bonded via a thiol group, and dihydrolipoic acid bonded via a thiol group, and pharmaceutically acceptable salts thereof.

In a second aspect, the present invention relates to compounds of the formula (I)

wherein $X_1$ and $X_2$ independently represent O, NH or S,
$R_1$ and $R_2$ are independently selected from the group consisting of a $C_1$-$C_{30}$ hydrocarbyl group, an amino acid bonded via an amide bond or a peptide bonded via an amide bond each having up to 200 amino acids, the residue $X_1$ or $X_2$ conjugated to $R_1$ or $R_2$ in this case being NH, and hydrogen, it being preferred that not both of the residues $R_1$ and $R_2$ are H, wherein $R_3$ is a residue selected from the group consisting of —S—$R_6$, wherein $R_6$ is a $C_1$-$C_{30}$ hydrocarbyl group, at least one of the radicals $R_1$ and $R_2$ not being H when $X_1$ and $X_2$ are oxygen, —S—$CH_2$—$CH(NH_2)(COOH)$ (cysteine-S-yl), a homologue or derivative thereof (e.g. N-acetyl cysteine-S-yl), and a peptide having up to 200 amino acids which contains at least one amino acid radical having a thiol group, preferably a cysteine radical and is bonded via the thiol sulfur, preferably via the cysteine sulfur (peptide-S-yl)

and pharmaceutically acceptable salts thereof.

The present invention also relates to the use of these compounds for preparing a drug and drugs containing these compounds.

DETAILED DESCRIPTION OF THE INVENTION

Specifically, a first aspect of the invention relates to compounds of the formula (I) as defined above. These thiosuccinic acid compounds may be considered adducts of thiols to the double bond of a fumaric acid or a fumaric acid derivative. This addition is reversible. The present invention is based on the finding that this reversibility may be used to advantage to reduce the side effects of a fumaric acid therapy.

Without wishing to be bound by a certain theory, the inventors assume that, by separation of the $R_3$ group and a hydrogen atom on the adjacent carbon atom under physiological conditions, the compounds of the invention release the corresponding fumaric acid derivative such as a fumaric acid mono- or dialkyl ester ($X_1$=$X_2$=O; $R_1$+$R_2$=H or $C_{1-30}$ alkyl). Therefore, it is assumed that the effectiveness of the claimed thiosuccinic acids is due to the release of a fumaric acid derivative.

The thiosuccinic acid derivatives of the formula (I) are acid esters, amides and thioesters of succinic acid or mixed forms (when $X_1$ is not equal to $X_2$) which are substituted with a thiol ($R_3$) in position 2 (i.e. in α-position to a carboxyl group). In general, suitable thiols are all kinds of hydrocarbyl thiols, —SH-group-containing peptides or amino acids. Cysteine or a peptide or protein, respectively, which contains cysteine is preferred. The latter have the advantage that an endogenous, non-toxic molecule is released in addition to the fumaric acid derivative when the thiol is separated. Optionally, this molecule may have its own desirable therapeutic effects.

Suitable thiols may also be other molecules having SH groups. Preferred are the coenzyme A and fragments thereof, the acyl carrier protein and dihydrolipoic acid.

The $C_1$-$C_{30}$ hydrocarbyl group in the definitions of $R_1$, $R_2$ and $R_6$ is preferably selected from the group consisting of a straight-chain, branched or cyclic, optionally unsaturated, $C_1$-$C_{30}$ alkyl, straight-chain, branched or cyclic, optionally unsaturated, $C_1$-$C_{30}$ acyl, $C_5$-$C_{30}$ aryl, $C_5$-$C_{30}$ aralkyl or a $C_5$-$C_{30}$ heteroaryl containing 1 to 3 heteroatoms independently selected from N, S and O. Preferably it is a straight-chain, branched or cyclic, optionally unsaturated, $C_1$-$C_{30}$ alkyl.

The hydrocarbyl group may optionally be substituted with substituents selected from the group consisting of $C_1$-$C_4$ alkyl, $C_1$-$C_4$ alkoxy, $C_1$-$C_4$ alkylthio, mono-$C_1$-$C_4$-alkylamine, di-$C_1$-$C_4$-alkylamine, amino, HO, HS, nitro, cyano, halogen (F, Cl, Br, J), =O and carboxy.

The straight-chain, branched or cyclic, optionally unsaturated, $C_1$-$C_{30}$ alkyl is preferably a $C_1$-$C_{10}$ alkyl, even more preferably a $C_1$-$C_6$ alkyl. Examples of preferred groups are methyl, ethyl, n-propyl, isopropyl, n-butyl, sec-butyl, t-butyl, pentyl, cyclopentyl, 2-ethyl hexyl, hexyl, cyclohexyl, heptyl, cycloheptyl, octyl, vinyl, allyl, 2-hydroxyethyl, 2-hydroxypropyl, 3-hydroxypropyl, 2,3-dihydroxypropyl, 2-methoxyethyl, 2-methoxymethyl, 3-methoxypropyl and 2,3-dimethoxypropyl. Methyl or ethyl are most preferred.

The straight-chain, branched or cyclic, optionally unsaturated, $C_1$-$C_{30}$ acyl is preferably a $C_1$-$C_{20}$ acyl, more preferably a $C_2$-$C_{18}$ acyl. Preferred examples are acetyl, propionyl, oleyl, stearyl and decenyl. Longer-chain acyl residues such as stearyl, oleyl and decenyl are especially preferred for $R_6$.

According to the invention, an aryl group is understood to mean an aryl group which may optionally be substituted, especially an alkyl-substituted aryl group having 5 to 20 carbon atoms, preferably an aryl- or alkyl-substituted aryl group having 6 to 10 carbon atoms. Exemplary groups that may be mentioned are phenyl, methyl phenyl, ethyl phenyl, propyl phenyl, and butyl phenyl. Phenyl and t-butyl phenyl are preferred.

The $C_5$-$C_{30}$, preferably $C_5$-$C_{10}$ aralkyl group is preferably selected from the group consisting of benzyl and phenyl-substituted $C_1$-$C_4$ alkyl residues such as phenethyl, phenyl propyl and phenyl butyl.

A $C_5$-$C_{30}$ heteroaryl, preferably a $C_6$-$C_{10}$ heteroaryl group, is preferably understood to be aryl groups comprising 1 to 3 hetero atoms independently selected from N, S or O. Examples are furanyl, pyrrolyl, imidazolyl, pyridyl, indolyl and pyrimidinyl.

In a first embodiment, $X_1$ and $X_2$ are oxygen (diester). In a second embodiment, $X_1$ and $X_2$ are NH (diamide). In a third embodiment, either $X_1$ or $X_2$ may be oxygen, the remaining $X_1$ or $X_2$ being NH (ester amides).

At least one of the residues $R_1$ or $R_2$ may be a $C_1$-$C_{30}$ hydrocarbyl. The second residue $R_1$ or $R_2$ may optionally be H. It is preferred that not both of the residues $R_1$ and $R_2$ be H. Preferably, $R_1$ and $R_2$ are independently a $C_1$-$C_{30}$ hydrocarbyl as defined above. More preferably, both of $R_1$ and $R_2$ are a straight-chain or branched $C_1$-$C_{30}$ alkyl, preferably $C_1$-$C_4$ alkyl. More preferably, $R_1$ and $R_2$ are methyl or ethyl, $R_1$ and $R_2$ most preferably being the same and representing methyl or ethyl. In that case, $X_1$ and $X_2$ are most preferably oxygen.

When one or both of $X_1$ and $X_2$ are NH, the corresponding residue $R_1$ or $R_2$ may also be an amino acid bonded via an amide bond or a peptide bonded via an amide bond each having up to 200 amino acids. In that case, $R_1$ and/or $R_2$ preferably correspond to the formula $(-CHR_5-CO-NH)_a R_4$ wherein a is 1 to 100, preferably 1 to 10, $R_4$ is H or a $C_1$-$C_4$ alkyl and $R_5$ is a side chain of a natural or synthetic amino acid.

The side chains of the natural amino acids are selected from the side chains of Ala, Val, Leu, Ile, Trp, Phe, Met, Tyr, Thr, Cys, Asn, Gln, Asp, Glu, Lys, Arg, His, citrulline, Hcy, Hse, Hyp, Hyl, Orn, Sar and Me-Gly. Preferably, this is a polar, more preferably a charged side chain such as Glu, Lys or Arg.

If $R_1$ and/or $R_2$ are a peptide, this is preferably selected from functional peptides or fragments thereof such as peptide hormones, growth factors, cytokines, neurotransmitters, neuropeptides, antibody fragments, coagulation factors and cyclosporines as well as derivatives and fragments thereof. Said peptides may be purified from natural sources, recovered by recombination or synthesised in accordance with known methods. It is preferred to use synthetic peptides.

Coupling the fumaric acid body to such a functional peptide has the advantage that a directed transmission of the active ingredient "fumaric acid body" to target cells may be carried out via the peptide. The peptide portion of the amides of the invention then interacts with such target cells. At the same time, the peptide portion may have its own effect on the disease to be treated so that a combination therapy may be achieved in this case. However, a combination therapy and/or directed administration permits reducing the dose to be administered in a desirable, optionally even synergistic manner.

According to a preferred embodiment of the invention, the peptide residue may be a cyclosporine residue the cycle of which may be cleaved at each peptide bond so as to make the fumaric acid-amide bond. According to the invention, generally all cyclosporines may be bonded to the fumaric acid body via an amide bond. Since cyclosporines are cyclic peptides, the peptide ring of the cyclosporine is generally cleaved at any location (at any amide bond) so as to obtain a linearised cyclosporine capable of entering into an amide bond. This is preferably cyclosporine A linearised before position 1.

The term "peptide hormones" as used in the present specification refers to physiologically highly active peptides which have the action of a hormone or act in a similar manner as a hormone and comprise up to 100 amino acids. Examples that may be mentioned are the glandular peptide hormones of the hypophysis such as corticotropin, follitropin, lutropin, melanotropin, prolactin, somatotropin, thyrotropin, oxytocin and vasopressin, the releasing hormone and inhibiting factors of the hypothalamus, the peptide hormones from the pancreas, stomach or intestine such as the glucagon, insulin, somatostatin, secretin, gastrin and cholecystokinin, the peptide hormones of the thyroid such as calcitonin, parathyrin and such like.

The term "growth factors" describes hormone-like peptides and proteins which promote cell division and cell differentiation, ensure growth and organ development and are needed for wound healing. Examples are colony-stimulating factors, the epidermal growth factor (EGF), erythropoietin, fibroblast growth factors, haematopoietic growth factors, hepatocycle growth factors, insulin and insulin-like growth factors, platelet-derived growth factor (PDGF), thrombopoietin, transforming growth factors, viral growth factors, but also interleukins.

The term "cytokins" as used here refers to polypeptides which are secreted by cells and may influence the function of other, usually adjacent cells after binding to specific receptors. Cytokins primarily regulate the complex interaction of the cells of the immune system. Examples of such cytokins that may be mentioned are interferons, interleukins, chemokins or colony-stimulating factors.

The term "neurotransmitter" refers to messenger substances which cause the transmission of signals or information by the chemical route on the synapses of the nervous system. Depending on the chemical composition of such neurotransmitters, we distinguish between amino acids such as glutamic acid, amino acid derivatives such as acetylcholine, monoamines such as the catechol amines, for example L-noradrenaline, the L-adrenaline and dopamine, serotonin and peptides. Accordingly, a sub-group of the neurotransmitters are the "neuropeptides" such as bradykinin, but also the enkephalin, endorphin etc.

The term "coagulation factors" as used here refers to proteins of the coagulation cascade. Likewise, the peptide to be coupled to the fumaric acid via an amide bond in the invention may be an antibody fragment, said fragment preferably also comprising a recognition sequence and/or binding sequence.

Fragments and/or derivatives of all the peptides mentioned above which are suitable for the invention may also be used. The term "fragment" refers to a portion of the above-mentioned peptides which is capable of amide bonding. Preferably, such a portion comprises recognition sequences for mediating a bonding to a cell receptor and/or an active centre for transmitting an active function.

The term "derivative" refers to a peptide which may be derived from the above-mentioned peptides and/or fragments by homologous substitution, deletion or insertion of one or more amino acid(s) into or from the peptide chain.

As far as the thiol residue $R_3$ is concerned, this may represent a $C_1$-$C_{30}$ hydrocarbyl group $R_6$ as defined above, which is bonded to the succinic acid via a sulfur atom, a cysteine-S-yl or a peptide bonded via a cysteine sulfur. It is also preferred that $R_3$ be homocysteine or a derivative thereof. The thiol residue $R_3$ may also be coenzyme A or a fragment thereof, an acyl carrier protein and dihydrolipoic acid.

The peptides that may form the residue $R_3$ are not subject to any restrictions as long as they contain an amino acid residue with a thiol group and preferably a cysteine residue. They are preferably selected from the above-mentioned functional peptides and fragments and derivatives thereof. In that case, $R_3$ more preferably corresponds to the formula wherein
b is in the range of 0 to 150, preferably 1 to 10,
c is in the range of 0 to 150, preferably 1 to 10, it being prohibited that b and c are both 0 at the same time,
each of the residues $R_5$ are independently as defined above, it being possible for the peptide bond being formed via a side-chain nitrogen if $R_5$ is a side chain of Lys, Arg, Gln or Asn, and pharmaceutically acceptable salts thereof. The invention also comprises stereoisomers (enantiomers or diastereomers), since the claimed molecules have at least one chiral centre.

Specific examples of such peptides are CRGQGTASSGN-VSDLA (hereinafter called CRG) (SEQ ID NO: 1), RVSLA-GACGVGGY (hereinafter called RVS) (SEQ ID NO: 2), IQQQRAMLC(CONH$_2$) (hereinafter called IQQ) (SEQ ID NO: 3) and KPNVTPTVAHRTSSSRVAVRSLVEFTC-CRAGALDWVCARRGR (hereinafter called KPN) (SEQ ID NO: 4).

Most preferably, the peptide residue $R_3$ is a glutathione which is bonded to the succinic acid via the cysteine sulfur. In turn, the mono- and diesters are preferred among these glutathione-S-yl succinic acid derivatives. Especially preferred compounds are the dimethyl-α-glutathione-S-yl succinic acid diesters, diethyl-α-glutathione-S-yl succinic acid diesters and methyl-ethyl-α-glutathione-S-yl-succinic acid diesters.

Alternatively, $R_3$ may be a cysteine-S-yl residue, a homologue or derivative thereof. Derivatives within the meaning of the present invention are especially cysteine radicals which are mono- or di-$C_{1-4}$-alkylated or mono- or di-$(C_{1-4})$-acylated at the amino nitrogen or esterified with a $C_{1-4}$ alkyl at the carboxyl group. However, derivatives may also be homologues of the cysteine and derivatives thereof which have been alkylated, esterified and acylated as described above. Examples that may be mentioned are N—$C_{1-4}$ acyl cysteine, preferably N-acetyl cysteine, N—$C_{1-4}$ alkyl cysteine, N,N-Di-$C_{1-4}$ alkyl cysteine and cysteine $C_{1-4}$ alkyl ester.

Most preferred are compounds of the formula (I) wherein $R_3$ is —S—CH$_2$—CH(NH$_2$)(COOH) (cysteine-S-yl) or N-acetyl cysteine-S-yl. In turn, the mono- and diesters are preferred among these cysteine-S-yl succinic acid derivatives. Especially preferred compounds are dimethyl-α-cysteine-S-yl succinic acid diester, diethyl-α-cysteine-S-yl succinic acid diester and methyl ethyl-α-cysteine-S-yl succinic acid diester. These correspond to the formula III and IV, respectively.

(III)

IV

Also preferred are compounds of the formula (I) wherein $R_3$ is coenzyme A and fragments thereof, acyl carrier protein, dihydrolipoic acid or homocysteine or a derivative of all these. Also included are salts of these compounds. The preferred compounds are represented by the formulae V to VIII.

Formula V:
2-Thiosuccinylwherein $X_1$ and $X_2$ are independently O or NH, wherein $R_1$ or $R_2$ are independently H, $C_1$-$C_{30}$ alkyl, $C_1$-$C_{30}$ aryl, $C_1$-$C_{30}$ dialkyl, $C_1$-$C_{30}$ diaryl or $C_1$-$C_{30}$ aralkyl and wherein $R_7$ is H or H$_2$PO$_3$.

Preferred fragments of the compound of the formula V are the dephospho-coenzyme A fragment, cysteamine fragment, β-alanyl cysteamine fragment, pantetheine fragment or phosphopantetheine fragment.

Formula VI:

wherein $X_1$ and $X_2$ are independently O or NH, wherein $R_1$ or $R_2$ are independently H, $C_1$-$C_{30}$ alkyl, $C_1$-$C_{30}$ aryl, $C_1$-$C_{30}$ dialkyl, $C_1$-$C_{30}$ diaryl or $C_1$-$C_{30}$ aralkyl and wherein $R_8$ is O-serine or O-serine in the acyl carrier protein.

Formula VII:

wherein at least one of $X_4$ and $X_5$ is a 2-thiosuccinyl residue of the formula (I) and, unless $X_4$ and $X_5$ both are a 2-thiosuccinyl residue of the formula (I), the other of $X_4$ or $X_5$ is SH, wherein, in formula (I), $X_1$ and $X_2$ are independently O or NH and wherein $R_1$ or $R_2$ are independently H, $C_1$-$C_{30}$ alkyl, $C_1$-$C_{30}$ aryl, $C_1$-$C_{30}$ dialkyl, $C_1$-$C_{30}$ diaryl or $C_1$-$C_{30}$ aralkyl and wherein $R_9$ is OH, O-alkyl, O-aryl, $NH_2$, NH-amide, N-diamide, NH amino acid, NH peptide or NH protein.

Formula VIII:

wherein A is a 2-thiosuccinyl residue of the formula (I) and, in formula (I), $X_1$ and $X_2$ are independently O or NH and wherein $R_1$ or $R_2$ are independently H, $C_1$-$C_{30}$ alkyl, $C_1$-$C_{30}$ aryl, $C_1$-$C_{30}$ dialkyl, $C_1$-$C_{30}$ diaryl or $C_1$-$C_{30}$ aralkyl and wherein $R_{10}$ and $R_{11}$ are independently H, OH or an amide with any other amino acid or acyl or O-alkyl.

The invention also comprises proteins or peptides containing one or more thiols, preferably cysteines, at least one, preferably several, thiol groups (a cysteine) of which are added to the double bond of a fumaric acid derivative with its/their sulfur atom. Preferred examples are serum albumin, such as HSA, BSA or immunoglobulins.

In addition, the present invention provides the use of the compounds of the formula (I) as drugs. The compounds of the formula (I) may preferably be used for preparing a pharmaceutical composition:

for the therapy of an autoimmune disease selected from the group consisting of polyarthritis, also called rheumatoid arthritis, multiple sclerosis, graft-versus-host reactions, juvenile-onset diabetes, Hashimoto's thyroiditis, Grave's disease (Basedow disease), systemic Lupus erythematodes (SLE), Sjogren's syndrome, pernicious anaemia and chronic active (=lupoid) hepatitis;

for use in transplantation medicine;

for the therapy of mitochondrial diseases selected from the group consisting of Parkinson syndrome, Alzheimer's disease, Chorea Huntington disease, retinopathia pigmentosa or forms of mitochondrial encephalomyopathies; as well as for the therapy of NF-kappaB mediated diseases selected from the group consisting of progressive systemic sclerodermia, osteochondritis syphilitica (Wegener's disease), cutis marmorata (livedo reticularis), Behcet disease, panarteritis, colitis ulcerosa, vasculitis, osteoarthritis, gout, arteriosclerosis, Reiter's disease, pulmonary granulomatosis, types of encephalitis, endotoxic shock (septic-toxic shock), sepsis, pneumonia, encephalomyelitis, anorexia nervosa, hepatitis (acute hepatitis, chronic hepatitis, toxic hepatitis, alcohol-induced hepatitis, viral hepatitis, jaundice, liver insufficiency and cytomegaloviral hepatitis), Rennert T-lymphomatosis, mesangial nephritis, post-angioplastic restenosis, reperfusion syndrome, cytomegaloviral retinopathy, adenoviral diseases such as adenoviral colds, adenoviral pharyngoconjunctival fever and adenoviral ophthalmia, AIDS, Guillain-Barré syndrome, post-herpetic or post-zoster neuralgia, inflammatory demyelinising polyneuropathy, mononeuropathia multiplex, mucoviscidosis, Bechterew's disease, Barett oesophagus, EBV (Epstein-Barr virus) infection, cardiac remodeling, interstitial cystitis, diabetes mellitus type II, radiosensitisation of malignant tumours, multi-resistance of malignant cells to chemotherapeutic agents (multidrug resistance in chemotherapy), granuloma annulare and cancers such as mamma carcinoma, colon carcinoma, melanoma, primary liver cell carcinoma, adenocarcinoma, kaposi's sarcoma, prostate carcinoma, leukaemia such as acute myeloid leukaemia, multiple myeloma (plasmocytoma), Burkitt lymphoma and Castleman tumour, for the therapy of psoriasis, psoriatic arthritis, neurodermitis and enteritis regionalis Crohn, for the therapy of cardiac insufficiency, especially left-ventricular failure, cardiac infarction, as a drug against cardiac arrest (cardioplebicum), as an anti-ischaemic drug and as a drug against angina pectoris, for the therapy of chronic obstructive pulmonary diseases and asthma, especially job-induced or stress-induced asthma or asthma cardiale and for inhibiting the cell proliferation of the non-striated muscles of the bronchi.

According to the invention, it is possible to use a combination of two or more of the above-mentioned compounds.

Even though the compounds of the formula (I) are not limited to certain stereomers such as enantiomers or diastereomers, those stereomers producing a fumaric acid derivative instead of a maleic acid derivative when $R_3$ and H are separated are preferred. However, the effectiveness is not limited to certain polymorphs, enantiomers or diastereomers of the claimed compound. Quite the opposite—both enantiomers resulting from the chirality centre of the carbon atom of succinic acid, which centre is linked to $R_3$, are expressly included in the invention.

The compounds of the invention may be prepared by addition. In general, addition may be carried out according to the following scheme:

Suitable mechanisms of addition are the nucleophilic addition (or Michael addition), the electrophilic addition or the free-radical addition. These reactions are known and described, for example, in "Organic Chemistry of Sulfur", edited by S. Oae, Plenum Press, New York and London. In each case, the corresponding fumaric acid derivative which is converted into a succinic acid derivative of the formula (I) by the addition of the thiol acts as the unsaturated compound. Preparation by addition is a preferred method of production, but other methods known to the person skilled in the art may be used, too.

In case of nucleophilic addition, the thiol is deprotonated under basic conditions and the thiolate anion added to the fumaric acid derivative. This type of addition is also called Michael addition. Suitable reaction conditions are obvious to the person skilled in the art and may be selected by routine experimentation.

In case of an electrophilic addition, the fumaric acid derivative is deprotonated and the thiol reacts with the carbocationic interim stage. The reaction conditions for this type of reaction are also obvious to a person skilled in the art and may be determined by routine experimentation.

If it is intended to prepare a compound of the invention wherein $R_3$—H is cysteine or linked to the succinic acid derivative via a cysteine residue, the nucleophilic or electrophilic addition of the cysteine radical to the fumaric acid derivative is the method of choice. A suitable solvent such as DMSO or THF and a basic catalyst such as an amine, preferably trimethyl amine or triethyl amine, may be used for the nucleophilic addition. However, the reaction may also be carried out in an aqueous medium using a mild base. If it is intended to carry out the electrophilic addition, it is recommended to use an acid, a Lewis acid or halogenated acid, as the catalyst. Thionyl chloride is preferred.

In a further aspect, the present invention finally relates to a drug comprising one or more of the compounds of the formula (I), preferably as the only active ingredient. It is preferred that the drug be present in a form suitable for injection. The drug may also be present in a form suitable for oral, rectal, transdermal, opthalmological, nasal or pulmonary administration. In addition to the active ingredient, the drug may contain the usual adjuvants.

For oral administration, the drug may be present, for example, in the form of tablets, coated tablets, capsules, granulate, solutions for drinking, liposomes, nano-particles, nano-capsules, micro-capsules, micro-tablets, pellets or powders as well as granulate filled in capsules, micro-tablets filled in capsules, pellets filled in capsules, nano-particles filled in capsules or powder filled in capsules. The drug is preferably present in the form of nano-particles, micro-pellets or micro-tablets which may optionally be filled into sachets or capsules. These micro-pellets or micro-tablets usually have a diameter (without coating) of about ≦5000 μm, preferably 300 to 2000 μm.

All of the solid oral dosage forms may preferably be provided with an enteric coating. This may be applied, for example, to the tablets, micro-tablets, micro-pellets, etc., or may be applied to the capsules containing the same.

As a matter of principle, the drug forms of the invention may be prepared by the classic tabletting method, but also by direct tabletting and as solid dispersions by the melting method or the spray drying method. If desired, an enteric coating may be applied by known processes in a classic coating pan or a fluid bed device. After drying is completed, a film coat may be applied in the same apparatus. When a mixture of active ingredients is used, it is possible to prepare pellets of the individual active ingredients and to mix these in the desired quantity, optionally after providing them with a film coat.

In case of parenteral application, the drug is available in a suitable form, for example as a sterile solution or emulsion. The correct formulations and suitable adjuvants are known to the person skilled in the art. A physiological salt solution that may optionally be buffered with phosphate is suitable for parenteral administration by injection, for example. The solution for injection may also contain stabilisers such as human serum albumin or PVP, means for adjusting osmolality such as mannitol, buffers such as citrate, phosphate or carbonate, and such like. Liposome or vesicle formulations are also suitable.

The drug of the invention contains an amount of the compound(s) according to the invention which is appropriate for the therapeutic purpose. This amount may be determined by the person skilled in the art by routine experimentation. As a rule, the drug will contain an amount of succinic acid derivatives which corresponds to 10 to 500 mg of fumaric acid, preferably 30 to 200 mg of fumaric acid, and most preferably 100 mg of fumaric acid.

In comparison with the known pharmaceutically active fumaric acid derivatives, the use of the succinic acid derivatives of the invention has the advantage that they are generally tolerated more easily. Therefore, the succinic acid derivatives of the invention are suitable for all common forms of administration, especially for injections. In particular, the uses according to the invention are less irritating and therefore cause fewer side effects.

The invention will now be illustrated, but not limited by the following examples.

EXAMPLES

Example 1

Figure 1:
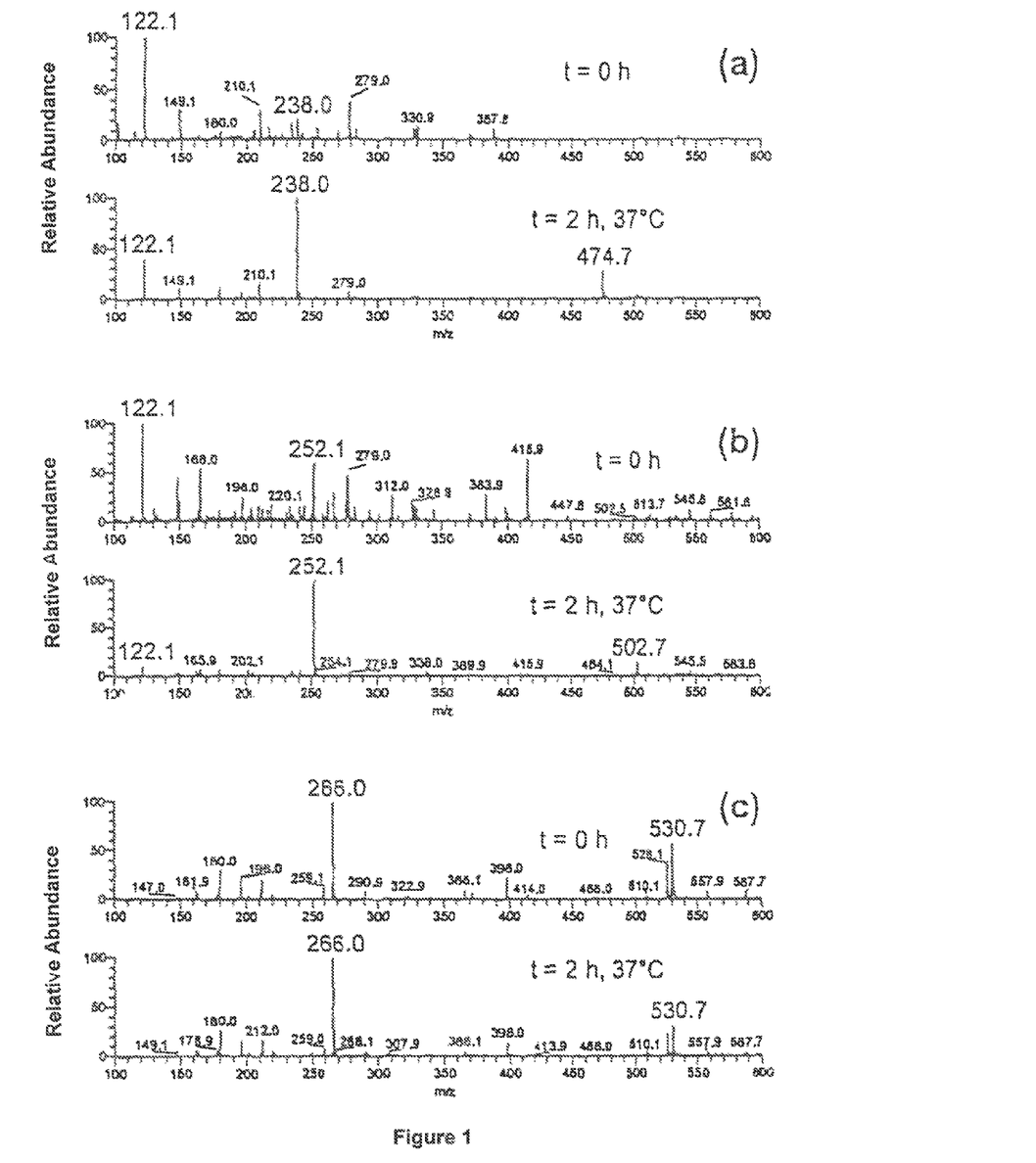
FIG. 1: ESI/MS mass spectra of the reaction product of a) fumaric acid, b) monomethyl fumarate and c) dimethyl fumarate with cysteine after mixing and 2 hours of stirring in each case.
Figure 2:
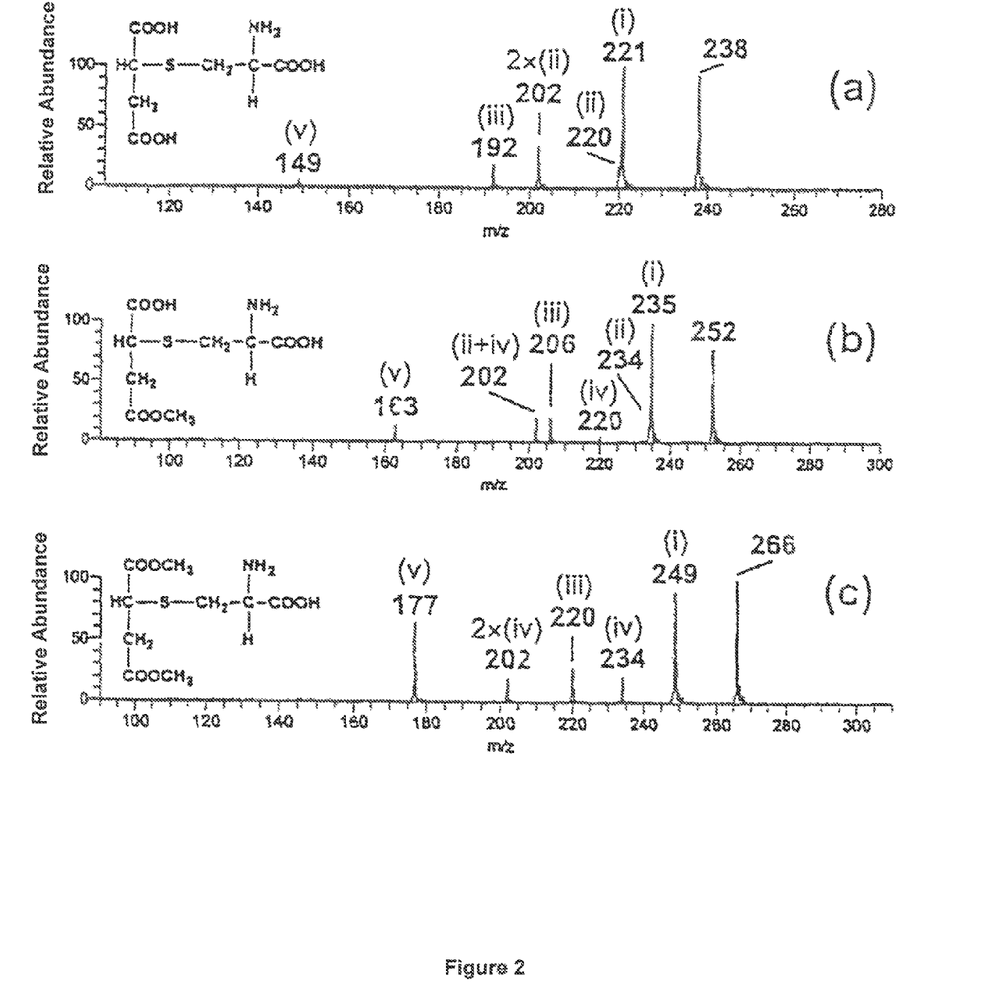
FIG. 2: Structure and fragmentation spectra of the products of the interaction of a) fumaric acid, b) monomethyl fumarate and c) dimethyl fumarate with cysteine.

A tenfold excess of a fumaric acid derivative A is mixed with a 0.01 M aqueous ammonium acetate solution at a pH of 7.4 and a 0.001 M thiol solution B at 37° C. Immediately after mixing and after two hours of stirring, a mass spectrum was taken. The fumaric acid derivatives and thiols, respectively, and the products to be expected are shown in table 1. The mass spectra recorded are shown in FIG. 1 and FIG. 2

All mass spectra were recorded by means of a LCQ Ion Trap mass spectrometer (Finnigan MAT, USA) equipped with an electrospray ioniser (ESI) and a chemical atmospheric pressure ionising interface (APCI), and a Reflex IV Time-of-Flight (TOF) mass spectrometer (Bruker, Germany) equipped with a matrix-supported laser desorption/ionisation (MALDI).

TABLE 1

| Example No. | A | B | Product | MS spectrum |
|---|---|---|---|---|
| 1 | FA[1] | Cysteine | α-Cysteine-S-yl succinic acid | 1a, 2a |
| 2 | MHF[2] | Cysteine | Methyl-α-cysteine-S-yl succinic acid ester | 1b, 2b |
| 3 | DMF[3] | Cysteine | Dimethyl-α-cysteine-S-yl succinic acid ester | 1c, 2c |
| 4 | DMF | GRG | Peptide | — |
| 5 | DMF | RVS | Peptide | — |
| 6 | DMF | IQQ | Peptide | — |
| 7 | DMF | KPN | Peptide | — |

[1] FA = fumaric acid
[2] MHF = monomethyl fumarate
[3] DMF = dimethyl fumarate

The shifts of the peaks of the peptide-DMF adducts vis-à-vis the peptides are shown in table 2.

TABLE 2 b and y ions in CID spectra of CRG, CRG~DMF, IQQ~DMF and compounds thereof.

| | $b_n^+$ | | | $b_n^{2+}$ | | | $y_n^-$ | | |
|---|---|---|---|---|---|---|---|---|---|
| n | CRG | CRG-DMF | Δ m/z (Th) | CRG | CRG-DMF | Δ m/z (Th) | CRG | CRG-DMF | Δ m/z (Th) |
| 2 | | 404.20 | | | | | | | |
| 3 | | | | | | | 318.07 | | |
| 4 | 445.13 | 589.27 | 144.14 | | | | 405.13 | 405.00 | −0.13 |
| 5 | | 646.13 | | | | | 504.00 | 504.20 | 0.20 |
| 6 | 603.40 | 747.40 | 144.00 | | | | 618.20 | 616.27 | 0.07 |
| 7 | 674.07 | 818.27 | 144.20 | | | | 675.20 | 675.20 | 0.00 |
| 8 | 761.27 | 905.27 | 144.00 | | | | 762.33 | 762.20 | −0.13 |
| 9 | 846.47 | 992.33 | 143.86 | | | | 849.13 | 849.20 | 0.07 |
| 10 | 905.20 | 1 049.40 | 144.20 | | | | 920.33 | 920.27 | −0.06 |
| 11 | 1 019.53 | 1 163.47 | 143.94 | | | | | 1 021.53 | |
| 12 | 1 118.33 | 1 262.33 | 144.00 | 559.80 | 631.67 | 71.87 | 1 078.47 | 1 078.33 | −0.14 |
| 13 | 1 205.33 | 1 349.40 | 144.07 | 603.40 | 675.20 | 71.80 | 1 206.53 | | |
| 14 | | | | 660.67 | 732.73 | 72.06 | 1 263.27 | 1 263.33 | 0.06 |
| 15 | | | | 717.27 | 789.33 | 72.06 | | | |

| | IQQ | IQQ-DMF | Δ m/z (Th) | IQQ | IQQ-DMF | Δ m/z (Th) | IQQ | IQQ-DMF | Δ m/z (Th) |
|---|---|---|---|---|---|---|---|---|---|
| 1 | | | | | | | | 265.00 | |
| 2 | 242.20 | 241.92 | −0.28 | | | | 234.00 | 378.10 | 144.10 |
| 3 | 370.07 | | | | | | 365.07 | 509.09 | 144.02 |
| 4 | 498.13 | 498.25 | 0.12 | | | | 436.20 | 580.14 | 143.94 |
| 5 | 654.53 | 654.39 | −0.14 | | | | | | |
| 6 | 725.47 | 725.44 | −0.03 | | | | | | |
| 7 | 858.40 | 856.37 | −0.03 | 428.73 | 428.59 | −0.14 | 848.20 | 992.35 | 144.15 |
| 8 | | 969.46 | | 485.20 | 485.28 | 0.08 | | | |

Example 2

In order to rule out the possibility that the products of the interaction between the fumaric acid derivative and cysteine or the cysteine-containing peptide were generated during ionisation in the ion source, two control experiments were carried out.

Figure 3:
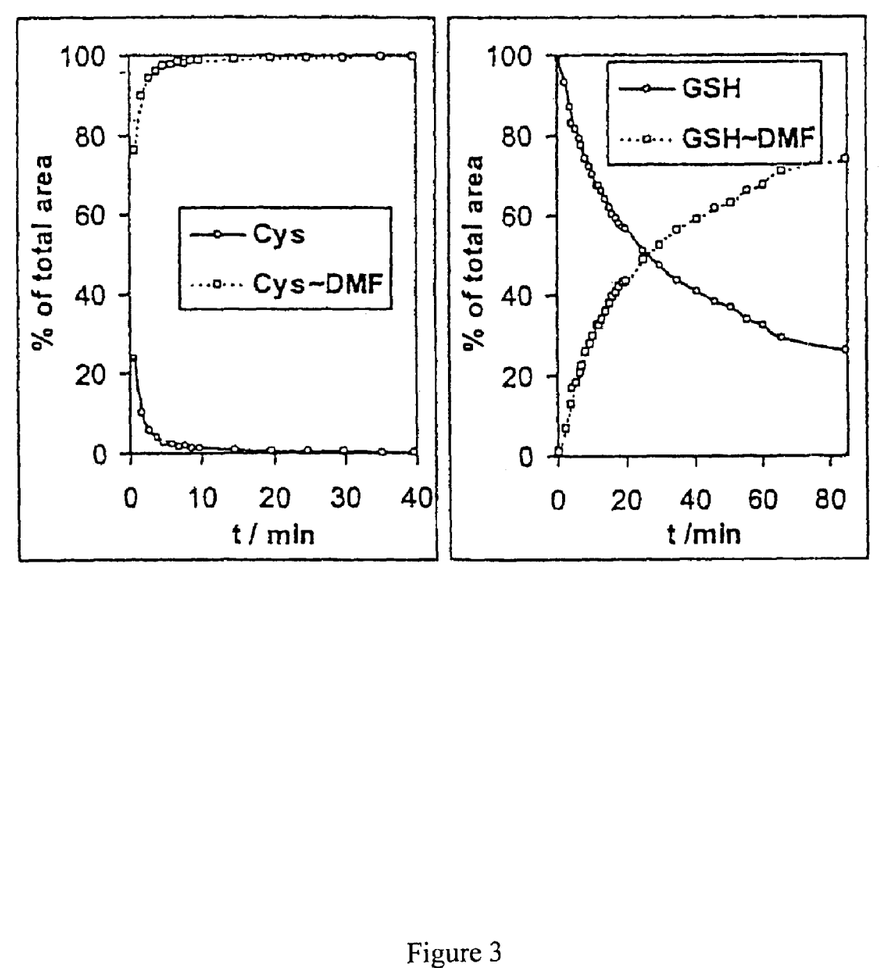
FIG. 3: Time dependence of the product formation in equimolar mixtures of cysteine and dimethyl fumarate and glutathione and dimethyl fumarate, measured by the flow injection APCI/MS (cysteine) and ESI/MS method.

In a first experiment, the solutions of cysteine or glutathion, respectively, were mixed with dimethyl fumarate and the time dependence of the increase or decrease of the reaction feedstock and products observed by flow injection analysis. For this purpose, samples were taken from each of the reaction mixtures of example 1 and injected into the carrier liquid stream and the ion source. The surfaces of the quasimolecular ion peaks were recorded as percent of the sum of the two compounds tracked vs. time. The result is shown in FIG. 3. It confirms the addition in solution. The spectra also confirm that the thiol group is added to the double bond of the fumaric acid.

Example 3

Dimethyl-2-(glutathione-S-yl)succinate

Glutathione (1 eq.) is dissolved in water and the pH value adjusted to 7.4 (with triethyl amine or ammonium acetate).

Dimethyl fumarate (1 eq.) dissolved in acetone is added over 20 to 30 minutes at approx. 40° C. The solution is stirred further over night and the solvent then distilled off or lyophilised, respectively. The residue is subjected to analysis and processed into the corresponding product.

ESI-MS-MS:

pos. ion mode: 490 [M+K]$^+$ (80); 474 [M+Na]$^+$ (100); 452 (M+H)$^+$ (78)

neg. ion mode: 901 [2M−H]$^-$ (5), 450 [M−H]$^-$ (100); 306 [M−(DMF+H)]$^-$ (20)

Example 4

Preparation of Film Tablets with an Enteric Coating Containing 100.0 mg of Dimethyl-2-(cysteine-S-yl)succinate Which Corresponds to 44 mg of Fumaric Acid Taking the necessary precautions (breathing mask, gloves, protective clothing, etc.), 10 kg of dimethyl-2-(cysteine-S-yl)succinate are crushed, mixed intensely and homogenised by means of a sieve 800. Then an excipient mixture of the following composition is prepared: 21 kg of starch derivative (STA-RX 1500®), 2 kg of micro-crystalline cellulose (Avicel PH 101®), 0.6 kg of polyvinyl pyrrolidone (PVP, Kollidon® 25), 4 kg of Primogel®, 0.3 kg of colloidal silicic acid (Aerosil®).

The active ingredient is added to the entire powder mixture, mixed, homogenised by means of a sieve 200 and processed with a 2% aqueous solution of polyvinyl pyrrolidone (PVP, Kollidon® 25) in the usual manner into binder granules, and then mixed with the outer phase in a dry state. The latter consists of 2 kg of a so-called FST complex containing 80% of talcum, 10% of silicic acid and 10% of magnesium stearate.

Thereafter the mixture is pressed into convex tablets with a weight of 400 mg and a diameter of 10.0 mm by the usual method. Instead of these classic compaction methods, other methods such as direct compaction or solid dispersions according to the melting and spray drying method may also be used for preparing tablets.

Enteric Coating:

A solution of 2.25 kg of hydroxy propyl methyl cellulose phthalate (HPMCP, Pharmacoat HP® 50) is dissolved in a solvent mixture consisting of 2.5 liters of demineralised water, 13 liters of acetone (Ph. Helv. VII) and 13 liters of ethanol (94% by weight) and then 0.24 kg of castor oil (Ph. Eur. II) are added to the solution. The solution is poured or sprayed in portions onto the tablet cores in a coating pan in a conventional manner.

After appropriate drying, the film coating is applied. Said coating consists of a solution of 4.8 kg of Eudragit E 12.5%®, 0.34 kg of talcum (Ph. Eur.), 0.52 kg of titanium(VI) oxide Cronus RN 56®, 0.21 of coloured lacquer ZLT-2 blue (Siegle), and 0.12 kg of polyethylene glycol 6000 (Ph. Helv. VII) in a solvent mixture of 8.2 kg of 2-propanol (Ph. Helv. VII), 0.06 kg of glycerine triacetate (Triacetin®) and 0.2 kg of demineralised water. After homogenous distribution in the coating pan or the fluidised bed, the mixture is dried and polished in the usual manner.

Example 5

Preparation of Enteric-Coated Micro-Tablets in Capsules Containing 120.0 mg of Dimethyl-2-(glutathione-S-yl)succinate Which Corresponds to 31 mg of Fumaric Acid Taking the necessary precautions (breathing mask, gloves, protective clothing, etc.), 12 kg of dimethyl-2-(cysteine-S-yl)succinate are crushed and homogenised by means of a sieve 800. Then an excipient mixture of the following composition is prepared: 17.5 kg of starch derivative (STA-RX 1500®), 0.3 kg of micro-crystalline cellulose (Avicel® PH 101), 0.75 kg of polyvinyl pyrrolidone (PVP, Kollidon® 120), 4 kg of Primogel, 0.25 kg of colloidal silicic acid (Aerosil).

The active ingredient is added to the entire powder mixture, homogenised by means of a sieve 200, processed in the usual manner with a 2% aqueous solution of polyvinyl pyrrolidone (PVP, Kollidon® K25) to obtain a binder granulate and mixed in a dry state with the outer phase consisting of 0.5 kg of Mg stearate and 1.5 kg of talcum. Then the powder mixture is pressed by the conventional method into convex tablets with a gross mass of 10.0 mg and a diameter of 2.0 mm.

In order to provide the tablets with an enteric coating, portions of a solution of 2.25 kg of hydroxy propyl methyl cellulose phthalate (HPMCP, Pharmacoat® HP 50) are dissolved in a mixture of the following solvents: 13 l of acetone, 13.5 l of ethanol (94% by weight denatured with 2% ketone) and 1.5 l of demineralised water. 0.24 kg of castor oil are added as softening agent to the finished solution and applied in portions to the tablet cores in the usual manner.

After drying is completed, a suspension of the following composition is applied as a film-coat in the same apparatus: 0.34 kg of talcum, 0.4 kg of titanium(VI) oxide (Cronus® RN 56), 0.324 kg of coloured lacquer L red lacquer 86837, 4.8 kg of Eudragit E 12.5% and 0.12 kg of polyethylene glycol 6000 pH 11 XI in a solvent mixture of the following composition: 8.17 kg of 2-propanol, 0.6 kg of glycerine triacetate (Triacetin®) and 0.2 kg of demineralised water.

The enteric-coated micro-tablets are analysed to determine their ingredients and then filled into gelatine hard capsules up to the pertinent net weight and sealed.

Example 6

Preparation of Enteric-Coated Micro-Tablets in Capsules Containing 120.0 mg of Dimethyl-2-(acetyl cysteine-S-yl)succinate Which Corresponds to 45 mg of Fumaric Acid 12 kg of dimethyl-2-(acetyl cysteine-S-yl)succinate are crushed and homogenised as described above. Then an excipient mixture of the following composition is prepared: 23.2 kg of micro-crystalline cellulose (Avicel® PH 200), 3 kg of croscarmellose sodium (AC-Di-SOL-SD-711), 2.5 kg of talcum, 0.1 kg of anhydrous silica (Aerosil® 200) and 1 kg of magnesium stearate. The active ingredient is added to the entire powder mixture and subjected to homogenous mixing. Then the powder mixture is pressed by the direct tabletting method into convex tablets with a gross mass of 10.0 mg and a diameter of 2.0 mm. Then a solution of 0.94 kg of Eudragit® in isopropanol is prepared which also contains 0.07 kg of dibutyl phthalate. This solution is sprayed onto the tablets. After that, a dispersion of 17.32 kg of Eudragit® L D-55 and a mixture of 2.8 kg of micro-talcum, 2 kg of Macrogol 6000 and 0.07 kg of dimethicone is prepared in water and sprayed onto the tablet cores.

The enteric-coated micro-tablets are analysed to determine their ingredients and then filled into gelatine hard capsules up to the pertinent net weight and sealed.

Example 7

Preparation of a Dry Substance Mixture for Parenteral Administration Containing 20.0 mg of Dimethyl-2-(acetyl cysteine-S-yl)succinate Peparatio sicca.

Dimethyl-2-(acetyl cysteine-S-yl)succinate 20 mg

Mannitol (isotonisation, kyro-protector) 40 mg

Solvent.

Water for injection purposes in glass 1 ml

Using standard techniques, the above-mentioned ingredients are processed into a parenteral form of administration.

The invention claimed is:
1. A compound of the formula (I)

wherein $X_1$ and $X_2$ are independently chosen from O, NH, and S,
$R_1$ and $R_2$ are both methyl, and
$R_3$ is —S—$CH_2$—CH($NH_2$)(COOH) or N-acetylcysteine-S-yl,
or a pharmaceutically acceptable salt thereof.

2. The compound according to claim 1 wherein $X_1$ and $X_2$ are oxygen.

3. The compound according to claim 1, wherein $R_3$ is N-acetylcysteine-S-yl.

4. A pharmaceutical composition comprising a compound or a pharmaceutically acceptable salt thereof, as defined in claim 1.

5. The pharmaceutical composition according to claim 4, wherein the pharmaceutical composition is in a form suitable for oral, rectal, transdermal, dermal, ophthalmological, nasal, pulmonary, or parenteral application.

6. The pharmaceutical composition according to claim 4, wherein the pharmaceutical composition is in a form suitable for parenteral application.

7. The pharmaceutical composition according to claim 4, wherein the pharmaceutical composition is in a form chosen from tablets, coated tablets, capsules, granulates, solutions for drinking, liposomes, nano-particles, nanocapsules, micro-capsules, micro-tablets, pellets, powders, granulate filled in capsules, micro-tablets filled in capsules, pellets filled in capsules, nano-particles filled in capsules, and powder filled in capsules.

8. A method of treating a disease comprising administering to a patient in need of such treatment, a compound or a pharmaceutically acceptable salt thereof as defined in claim 1, wherein the disease is chosen from
an autoimmune disease chosen from polyarthritis, multiple sclerosis, graft-versus-host reactions, juvenile-onset diabetes, Hashimoto's thyroiditis, Grave's disease (Basedow disease), systemic Lupus erythematodes (SLE), Sjogren's syndrome, pernicious anaemia, and chronic active (=lupoid) hepatitis;
transplantation;
mitochondrial diseases chosen from Parkinson syndrome, Alzheimer's disease, Chorea Huntington disease, retinopathia pigmentosa, and forms of mitochondrial encephalomyopathies;
NF-kappaB mediated diseases chosen from progressive systemic sclerodermia, osteochondritis syphilitica (Wegener's disease), cutis marmorata (livedo reticularis), Behcet disease, panarteritis, colitis ulcerosa, vasculitis, osteoarthritis, gout, arteriosclerosis, Reiter's disease, pulmonary granulomatosis, types of encephalitis, endotoxic shock (septic-toxic shock), sepsis, pneumonia, encephalomyelitis, anorexia nervosa, hepatitis, Rennert T-lymphomatosis, mesangial nephritis, post-angioplastic restenosis, reperfusion syndrome, cytomegaloviral retinopathy, adenoviral diseases, adenoviral pharyngoconjunctival fever, adenoviral ophthalmia, AIDS, Guillain-Barré syndrome, post-herpetic or post-zoster neuralgia, inflammatory demyelinising polyneuropathy, mononeuropathia multiplex, mucoviscidosis, Bechterew's disease, Barett oesophagus, EBV (Epstein-Barr virus) infection, cardiac remodeling, interstitial cystitis, diabetes mellitus type II, radiosensitisation of malignant tumours, multi-resistance of malignant cells to chemotherapeutic agents (multidrug resistance in chemotherapy), granuloma annulare, and cancers;
psoriasis, psoriatic arthritis, neurodermitis, and enteritis regionalis Crohn;
cardiac insufficiency, left-ventricular failure, cardiac infarction, cardiac arrest (cardioplebicum), ischaemia, and angina pectoris; and
chronic obstructive pulmonary diseases and asthma.

9. The method of claim 8, wherein the disease is hepatitis and is selected from the group consisting of acute hepatitis, chronic hepatitis, toxic hepatitis, alcohol-induced hepatitis, viral hepatitis, jaundice, and cytomegaloviral hepatitis.

10. The method of claim 8, wherein the disease is an adenoviral disease that is an adenoviral cold.

11. The method of claim 8, wherein the disease is cancer and is selected from the group consisting of mamma carcinoma, colon carcinoma, melanoma, primary liver cell carcinoma, adenocarcinoma, kaposi's sarcoma, prostate carcinoma, leukaemia, acute myeloid leukaemia, multiple myeloma (plasmocytoma), Burkitt lymphoma, and Castleman tumour.

* * * * *